(12) United States Patent
Lu et al.

(10) Patent No.: US 9,649,466 B2
(45) Date of Patent: May 16, 2017

(54) SYSTEMS AND METHODS FOR GAS MIXTURE DELIVERY TO HUMANS INSIDE AN MRI SCANNER

(71) Applicant: Board of Regents, The University of Texas System, Austin, TX (US)

(72) Inventors: Hanzhang Lu, Coppell, TX (US); Peiying Liu, Towson, MD (US)

(73) Assignee: The Board of Regents of the University of Texas System, Austin, TX (US)

( * ) Notice: Subject to any disclaimer, the term of this patent is extended or adjusted under 35 U.S.C. 154(b) by 34 days.

(21) Appl. No.: 14/623,779

(22) Filed: Feb. 17, 2015

(65) Prior Publication Data
US 2015/0231357 A1 Aug. 20, 2015

Related U.S. Application Data

(60) Provisional application No. 61/941,145, filed on Feb. 18, 2014.

(51) Int. Cl.
| | |
|---|---|
| A61B 5/00 | (2006.01) |
| A61M 16/12 | (2006.01) |
| A61M 16/08 | (2006.01) |
| A61M 16/20 | (2006.01) |
| A61B 5/083 | (2006.01) |
| A61B 5/055 | (2006.01) |
| A61B 5/0205 | (2006.01) |
| A61B 5/024 | (2006.01) |
| A61B 5/08 | (2006.01) |

(52) U.S. Cl.
CPC .......... *A61M 16/122* (2014.02); *A61B 5/055* (2013.01); *A61B 5/0833* (2013.01); *A61B 5/0836* (2013.01); *A61M 16/0816* (2013.01); *A61M 16/20* (2013.01); *A61B 5/024* (2013.01); *A61B 5/0205* (2013.01); *A61B 5/0816* (2013.01); *A61M 2202/0208* (2013.01); *A61M 2202/0225* (2013.01); *A61M 2202/0266* (2013.01); *A61M 2230/432* (2013.01); *A61M 2230/435* (2013.01)

(58) Field of Classification Search
CPC .............. A61M 16/10; A61B 5/14551; A61B 5/14553; A61B 5/0205
See application file for complete search history.

(56) References Cited

U.S. PATENT DOCUMENTS

| | | | |
|---|---|---|---|
| 6,708,689 B2 | 3/2004 | Fisher | |
| 2009/0120435 A1 | 5/2009 | Slessarev et al. | |
| 2013/0006094 A1* | 1/2013 | Charles | A61B 5/055 600/411 |
| 2013/0225978 A1 | 8/2013 | Remmele et al. | |

(Continued)

OTHER PUBLICATIONS

PCT International Search Report and Written Opinion issued in International Application No. PCT/US2015/016082, mailed May 29, 2015.

(Continued)

*Primary Examiner* — Robert N Wieland
(74) *Attorney, Agent, or Firm* — Parker Highlander PLLC

(57) ABSTRACT

Systems and methods for delivery of gas mixtures to humans inside an MRI scanner, including while monitoring and recording physiological parameters.

28 Claims, 6 Drawing Sheets
(3 of 6 Drawing Sheet(s) Filed in Color)

(56) References Cited

U.S. PATENT DOCUMENTS

2016/0158481 A1* 6/2016 Klein .................. A61M 16/122
128/203.14

OTHER PUBLICATIONS

Skow et al., "Differential cerebrovascular CO2 reactivity in anterior and posterior cerebral circulations," *Respiratory Physiology & Neurobiology*, 189:76-86, 2013.

Wise et al., "Dynamic forcing of end-tidal carbon dioxide and oxygen applied to functional magnetic resonance imaging," *Journal of Cerebral Blood Flow & Metabolism*, 27(8):1521-1532, 2007.

Yezhuvath et al., "On the assessment of cerebrovascular reactivity using hypercapnia BOLD MRI," *NMR Biomed*, 22(7):779-786, 2009.

* cited by examiner

SYSTEMS AND METHODS FOR GAS MIXTURE DELIVERY TO HUMANS INSIDE AN MRI SCANNER

CROSS-REFERENCE TO RELATED APPLICATIONS

The present application claims benefit of priority to U.S. Provisional Application Ser. No. 61/941,145, filed Feb. 18, 2014, the entire contents of which are being hereby incorporated by reference.

GOVERNMENT LICENSE RIGHTS

This invention was made with government support under R01 NS067015 by the National Institute of Neurological Disorders and Stroke of the NIH. The government has certain rights in the invention.

BACKGROUND OF THE INVENTION

1. Field of the Invention

Exemplary embodiments of the present invention relate generally to the fields for delivery of gas mixtures to humans inside a magnetic resonance imaging (MRI) scanner. More particularly, exemplary embodiments concern systems and methods for delivery of gas mixtures to humans inside an MRI scanner while monitoring and recording physiological parameters.

2. Description of Related Art

Existing MRI scanners and associated systems do not readily provide for the administration of different combinations of breathing gasses to a human subject located inside the MRI scanner without moving the subject. The ability to administer different combinations of breathing gasses to a subject while conducting MRI scans without moving the subject can provide the ability to accurately measure many important physiological conditions, including for example, cerebrovascular reactivity (CVR), cerebral blood volume, and bolus transit time inside the blood stream.

CVR refers to the ability of blood vessels to dilate upon stimulation and is an important marker of brain's vascular function [1]. Cerebral blood volume (CBV) refers to the amount of blood in the brain. Bolus transit time refers to the time it takes for the gas bolus to travel from one location to another inside the brain's vascular network. There has been an increased interest in quantitative mapping of these physiological properties using MRI in combination with gas challenge. However, the application of this method is limited by the availability of MRI-compatible gas delivery systems.

Taking CVR, for example, the most commonly used method of CVR mapping is maneuvering the concentration of $CO_2$, a potent vasodilator, in the blood by hypercapnia inhalation while monitoring vascular responses using MRI. However, delivering $CO_2$ gas mixture to the subject inside the MRI scanner is not a trivial endeavor. Special considerations are required in designing MRI-compatible gas delivering systems. These special considerations include: (1) all components must be non-metallic, since metal cannot be used inside an MRI scanner; (2) the system should work within a small space that the MRI system and its head coil allow; (3) the system should work with a lying-down position (as MRI scanner requires) instead of sitting up, while keeping the subject comfortable; (4) the physiological parameters, such as end-tidal $CO_2$ ($EtCO_2$) and end-tidal $O_2$ ($EtO_2$), should be recorded accurately with seconds of timing accuracy and stored on a computer for any future use.

In view of these technical challenges, there are limited MRI-compatible gas delivery systems that have been reported to provide $CO_2$ maneuvering in MRI environment [17,18], each of which are complicated and expensive. In addition, these systems require extensive training of the operator and preparation time. The use of a face mask in such systems also dampens the accuracy of $EtCO_2$ and $EtO_2$ recordings as the inspired and expired air is mixed in the mask space where the sampling line is located. These issues largely limit CVR mapping from being a widely available tool in clinical practice.

Compared to baseline vascular parameters, such as baseline cerebral blood flow (CBF)—which can be influenced by factors unrelated to vascular function such as neural activity and metabolic demand—CVR is more specific in reflecting vascular health [2]. During the past few years, CVR measured with MRI has found to be attenuated in many brain disorders such as small vessel diseases [3], arteriovenous malformation [4], Moyamoya disease [5,6], arterial stenosis [7], drug-addictive conditions [8], and normal aging [9]. It has also been shown that CVR can be used to normalize functional MRI (fMRI) signal [10-14] and in the evaluation of brain metabolism [15,16].

SUMMARY

Embodiments disclosed herein include systems and methods that allow the delivery of special gas mixtures (e.g. any fraction of $O_2$, any fraction of $CO_2$, any fraction of $N_2$, any fraction of other gas that is safe for human to inhale, and their combination) to a human to breathe while he or she is lying inside an MRI scanner. Disclosed embodiments are economical, easier to use than existing systems and methods, and accurate in recording physiological information.

Furthermore, while a single hypercapnia challenge is typically used to quantify CVR, an additional hyperoxia challenge could provide additional information of cerebrovascular system and increase the conspicuity of true CVR abnormalities. Accordingly, embodiments disclosed herein also present a novel breathing paradigm, in which $CO_2$ and $O_2$ inhalation are applied concomitantly. Such an application can allow the acquisition of both $CO_2$ CVR and $O_2$ reactivity maps without adding scan time.

Experimental data has suggested exemplary embodiments of the disclosed systems and methods are feasible for both healthy subjects and patients. The $O_2$ reactivity map generated for "free" by the concomitant paradigm could be used to improve (correct or normalize) the $CO_2$ CVR map in detecting vascular abnormalities. Therefore, CVR mapping using the disclosed gas delivery system and concomitant $CO_2/O_2$ paradigm may be a practical and promising tool in clinical applications of cerebrovascular diseases.

Exemplary embodiments include a system for administering breathing gasses to a subject during a magnetic resonance imaging (MRI) scan. In certain embodiments, the system comprises: a plurality of containers containing one or more gasses; a multi-port valve in fluid communication with the plurality of containers; a conduit in fluid communication with the multi-port valve and a two-way non-rebreathing valve; a tube in fluid communication with the two-way non-rebreathing valve, a first sampling port and a second sampling port; and a mouthpiece in fluid communication with the tube.

In particular embodiments, at least one of the containers contains 5% $CO_2$ and 95% $O_2$; at least one of the containers contains 5% $N_2$ and 95% $N_2$; and at least one of the containers contains 5% $CO_2$, 21% $O_2$ and 74% $N_2$. In some embodiments, the plurality of containers are comprised of flexible containers. Specific embodiments further comprise a coupling mechanism configured couple to an MRI coil, where the coupling mechanism is configured to support the mouthpiece, the two-way breathing valve, and the tube from the MRI head coil.

In certain embodiments, the coupling mechanism is configured to couple the conduit to the MRI head coil, and in particular embodiments, the tube is a U-shaped tube. In some embodiments, the multi-port valve can be adjusted during use to adjust a mixture of the one or more gasses in fluid communication with the conduit. In specific embodiments, the one or more gasses comprises O2, CO2 and N2. In certain embodiments, the first sampling port is coupled to an O2 monitor and the second sampling port is coupled to a CO2 monitor. In particular embodiments, the O2 monitor is configured to measure end-tidal O2 levels and the CO2 monitor is configured to measure end-tidal CO2 levels, and wherein the end-tidal O2 level is measured independent of the end-tidal CO2 level.

In some embodiments, the multi-port valve is configured to allow room air to enter a port in the multi-port valve. Specific embodiments further comprise a nose clip. Some embodiments further comprise a first elbow coupling member coupled to the mouthpiece and the tube. Certain embodiments further comprise a second elbow coupling member coupled to the two-way non-rebreathing valve and the tube.

Exemplary embodiments include a method comprising: administering breathing gasses to a subject during a magnetic resonance imaging (MRI) scan; and monitoring a plurality of physiological parameters of the subject during the MRI scan, where the breathing gasses are administered to the patient via a system comprising: a plurality of containers containing one or more gasses; a multi-port valve in fluid communication with the plurality of containers; a conduit in fluid communication with the multiport valve and a two-way non-rebreathing valve; a tube in fluid communication with the two-way non-rebreathing valve, a first sampling port and a second sampling port; and a mouthpiece in fluid communication with the tube.

In certain embodiments, administering breathing gasses to a subject comprises administering gasses containing the following mixtures: 5% CO2 and 95% O2; 5% N2 and 95% N2; and 5% CO2, 21% O2 and 74% N2.

Particular embodiments further comprise coupling a coupling mechanism to an MRI head coil to support the mouthpiece, the two-way breathing valve, and the tube from the MRI head coil. Some embodiments further comprise coupling the conduit to the MRI head coil with the coupling mechanism. In specific embodiments, the tube is a U-shaped tube. Certain embodiments further comprise adjusting the multi-port valve to adjust a mixture of the one or more gasses in fluid communication with the conduit. In particular embodiments, the one or more gasses comprises O2, CO2 and N2. In some embodiments, O2 and CO2 gasses are applied concomitantly. Specific embodiments further comprise applying a nose clip to the subject to restrict the subject from breathing through his or her nose. In certain embodiments, a facemask is not applied to the subject. In particular embodiments, the first sampling port is coupled to an O2 monitor and the second sampling port is coupled to a CO2 monitor. Some embodiments further comprise measuring end-tidal O2 levels and measuring end-tidal CO2 levels, where the end-tidal O2 level is measured independently of the end-tidal CO2 level. Specific embodiments further comprise: generating a CO2 reactivity map; and generating an O2 reactivity map. Certain embodiments further comprise: using the CO2 reactivity map as a surrogate of cerebrovascular reactivity or cerebrovascular reserve for disease diagnosis and/or monitoring; and using the O2 reactivity map as a surrogate of cerebral blood volume for disease diagnosis and/or monitoring. Particular embodiments further comprise using the O2 reactivity map to normalize a CVR map to obtain a corrected CVR map.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
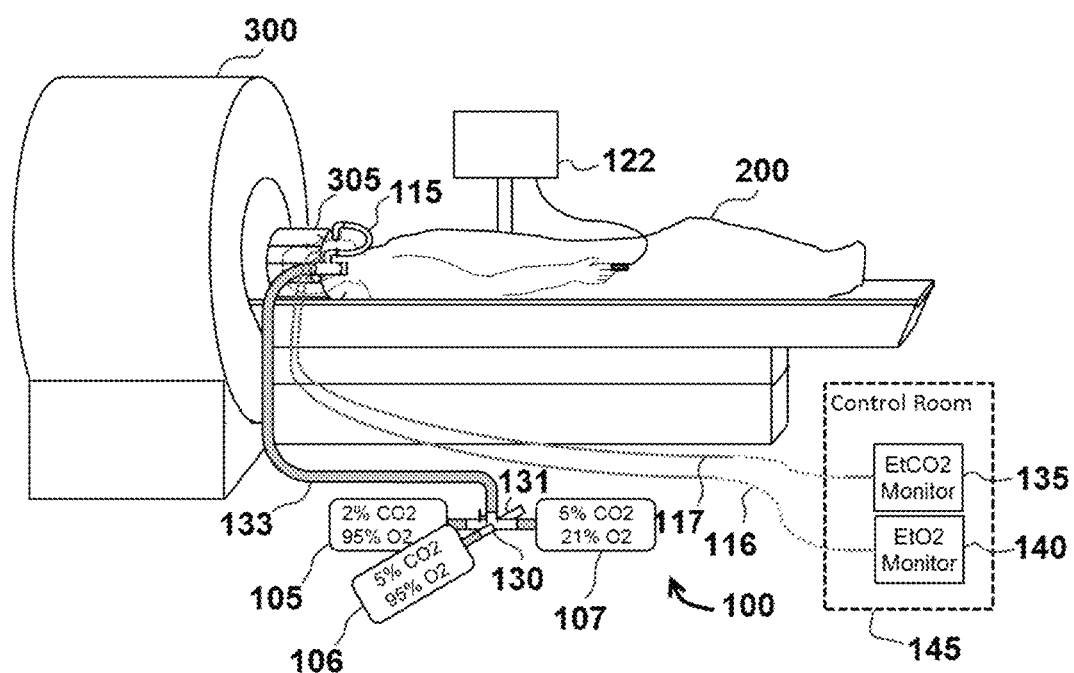
FIG. 1 shows a schematic of an MRI-compatible gas delivery system during use.
Figure 2:
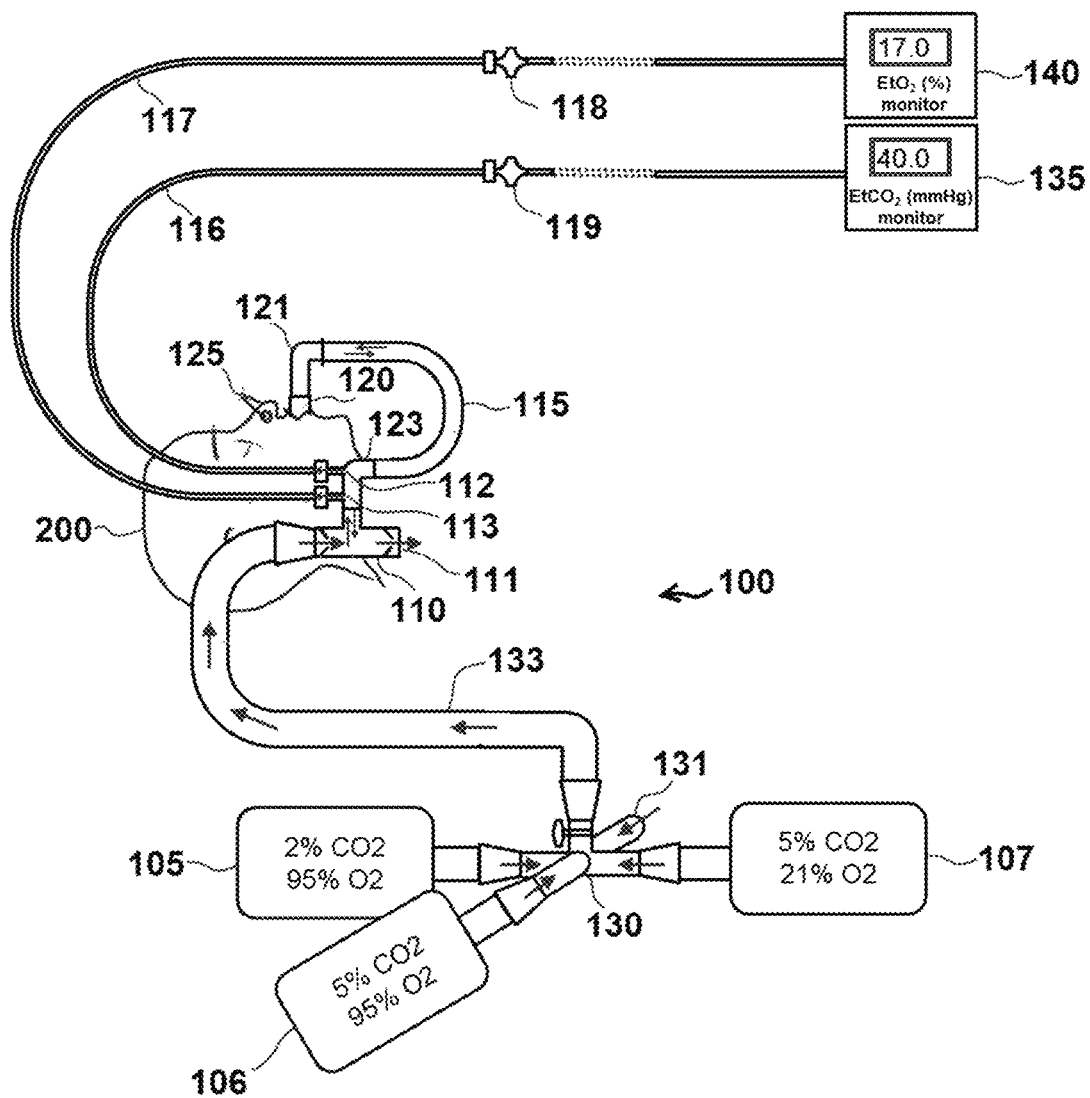
FIG. 2 shows a schematic of components of the system of FIG. 1.

Systems and methods to allow the delivery of special gas mixtures to a subject while located within an MRI scanner are disclosed herein. Referring initially to FIG. 1, a gas delivery system 100 is shown with a human subject 200 in preparation for an MRI scan by MRI scanning device 300. In exemplary embodiments of system 100, all parts inside the MRI scanner room are plastic to ensure the MRI compatibility. The special gas mixtures, for example the 5% CO2, 74% N2, and 21% O2, are contained within flexible containers 105, 106 and 107 (e.g. Douglas bags in certain embodiments) and delivered to subject 200 through a two-way non-rebreathing valve 110 (as shown in FIG. 2, which provides a more detailed schematic view of the components of system 100). Valve 110 can allow exhaled air to exit via port 111 in the embodiment shown.

Figure 3:
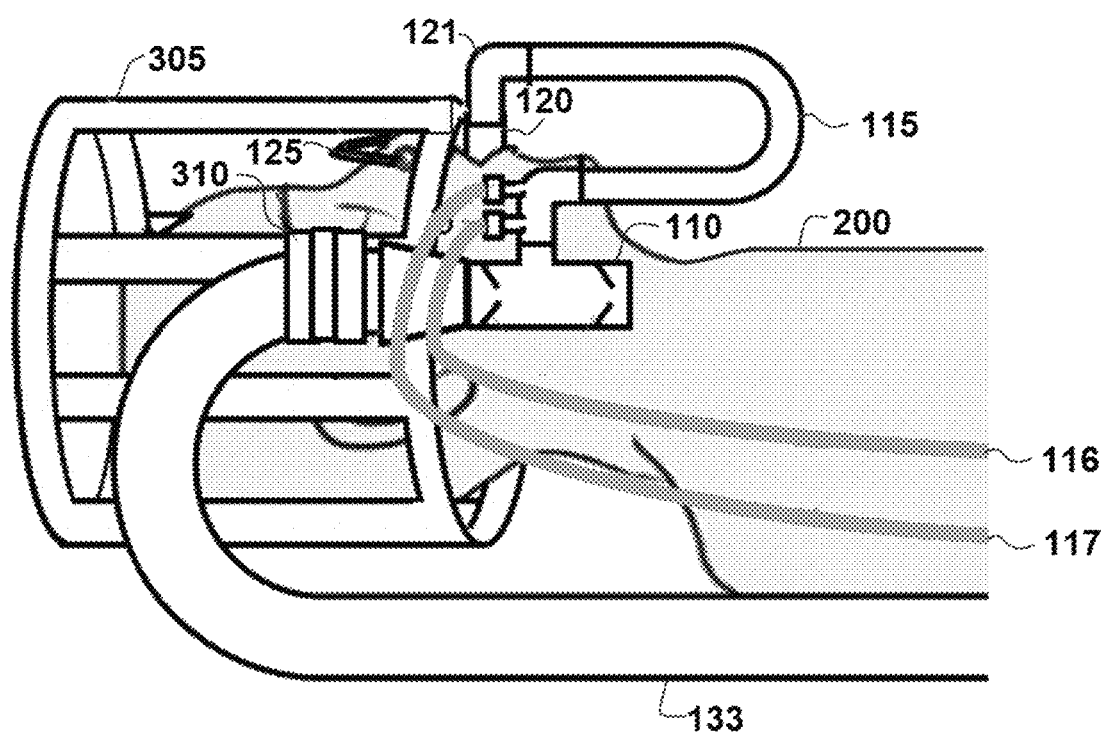
FIG. 3 shows a partial schematic of components of the system of FIG. 1.

Referring now to FIGS. 2 and 3, a schematic partial view of system 100 is shown during operation. For purposes of clarity, not all elements are labeled in all figures. A tube 115

(in this example, a U-shaped tube) is coupled to two-way non-rebreathing valve 110 on one end, and coupled to a mouthpiece 120 on the other end. In certain embodiments, one elbow coupling member 121 couples mouthpiece 120 and tube 115 and another elbow coupling member 123 couples two-way non-rebreathing valve 110 and tube 115. Tube 115 allows gas to be delivered to subject 200 in the tight space inside MRI head coil 305, and allows mouthpiece 120 to be more comfortably situated in the mouth of subject 200 while subject 200 is lying on the scanner table of MRI scanning device 300. This can allow subject 200 to hold mouthpiece 120 in position without having to bite down on mouthpiece 120.

In the embodiment shown, a portion of system 100 is also coupled to an MRI head coil 305 by a coupling mechanism 310. In certain embodiments, coupling mechanism 310 may comprise an adhesive, a hook-and-loop (e.g. Velcro®) arrangement, a hook, a snap, a button, or other configuration suited for coupling one or more components to MRI head coil 305. During use, MRI head coil 305 can support components of system 100, including for example, two-way non-rebreathing valve 110, tube 115 and mouthpiece 120. This can provide additional comfort to the subject and also reduce the effort exerted by the subject to support mouthpiece 120 and the associated components. This can further allow the subject to remain in position without moving, thereby improving the accuracy of the MRI scan by reducing motion artifact.

During an MRI scan, subject 200 is fitted with a nose clip 125 and breaths through the mouth. In exemplary embodiments of the method, an operator can switch a multi-port valve 130 (e.g. a five-way valve in the embodiment shown in FIG. 2) coupled to flexible containers 105, 106, and 107 to control the breathing of air (either room air or gas mixtures in flexible containers 105, 106 and 107). In the embodiment shown, room air can enter multi-port valve 130 via port 131, and multi-port valve 130 is coupled to valve 110 via conduit 133. Exemplary embodiments of system 100 allow an operator to manually adjust the inhaled breathing gas during testing by manipulating multi-port valve 130 without the need to reprogram control systems.

In certain embodiments, physiological parameters (e.g. end-tidal CO2 and O2 levels), can be recorded continuously on a computer during the scan using a CO2 monitor 135 (e.g. a capnograph device such as Capnogard, Philips Medical Systems, CT) and an O2 monitor 140 (e.g. O2100C, BIOPAC Systems, Inc., CA), respectively to monitor end-tidal CO2 and O2 levels. In specific embodiments, the parameters can be measured with sampling points 112, 113 on elbow member 123 (or other components, e.g. tube 115). Sampling points 112 and 113 can be coupled to conduits 116 and 117, which may include coupling members 118 and 119. In specific embodiments, coupling members 118 and 119 may be Luer locks or moisture-removing filters. In certain embodiments, CO2 monitor 135 and O2 monitor 140 may be located in a separate control room 145 outside the MRI scanner room. In addition, other parameters, including for example, breathing rate, heart rate, and arterial oxygenation saturation can also be monitored by a pulse-oximetry device 122 (generally available in all MRI rooms) and recorded continuously on the computer, including for example a laptop computer.

Accordingly, system 100 can provide a breathing regimen with hypercapnia, hyperoxia, and any other prepared gas with mixed CO2, O2 and N2 contents. In certain embodiments, a breathing regimen comprising CO2 and O2 administered both individually and concomitantly can be applied.

One advantage of having both CO2 and O2 maps is that one can use the O2-reactivity map to normalize the CVR map to obtain a "Corrected CVR map", which contains minimal influences of confounding factors such as the presence of large veins or different amount of blood present in gray vs. white matter. However, one concern of the normalized approach is that the scan duration may be increased by adding the O2 inhalation. Accordingly, exemplary embodiments include a novel gas challenge protocol that allows the concomitant measurement of CO2-CVR and O2-reactivity maps without adding scan time.

FIG. 4A shows a concomitant CO2-O2 paradigm. It should be noted that in this embodiment the application of CO2 and O2 simultaneously does not involve simply mixing the hypercapnia (5% CO2, 21% O2, and 74% N2) and hyperoxia (95% O2, and 5% N2) gas together. Instead, the disclosed regimen maintains the CO2 content identical to the CO2-only challenge and maintain the O2-content identical to the O2-only challenge, by reducing N2 content. Specifically, the simultaneous CO2/O2 challenge is achieved by using a new gas mixture containing 5% CO2, 95% O2, and 0% N2.

As can be seen in FIG. 4B, the concomitant CO2/O2 challenge could provide the CO2 and O2 maneuvering independently as if they are achieved separately. The corresponding BOLD signal recorded the sum effect of CO2 and O2 maneuvering.

Experimental Data

Figure 4:
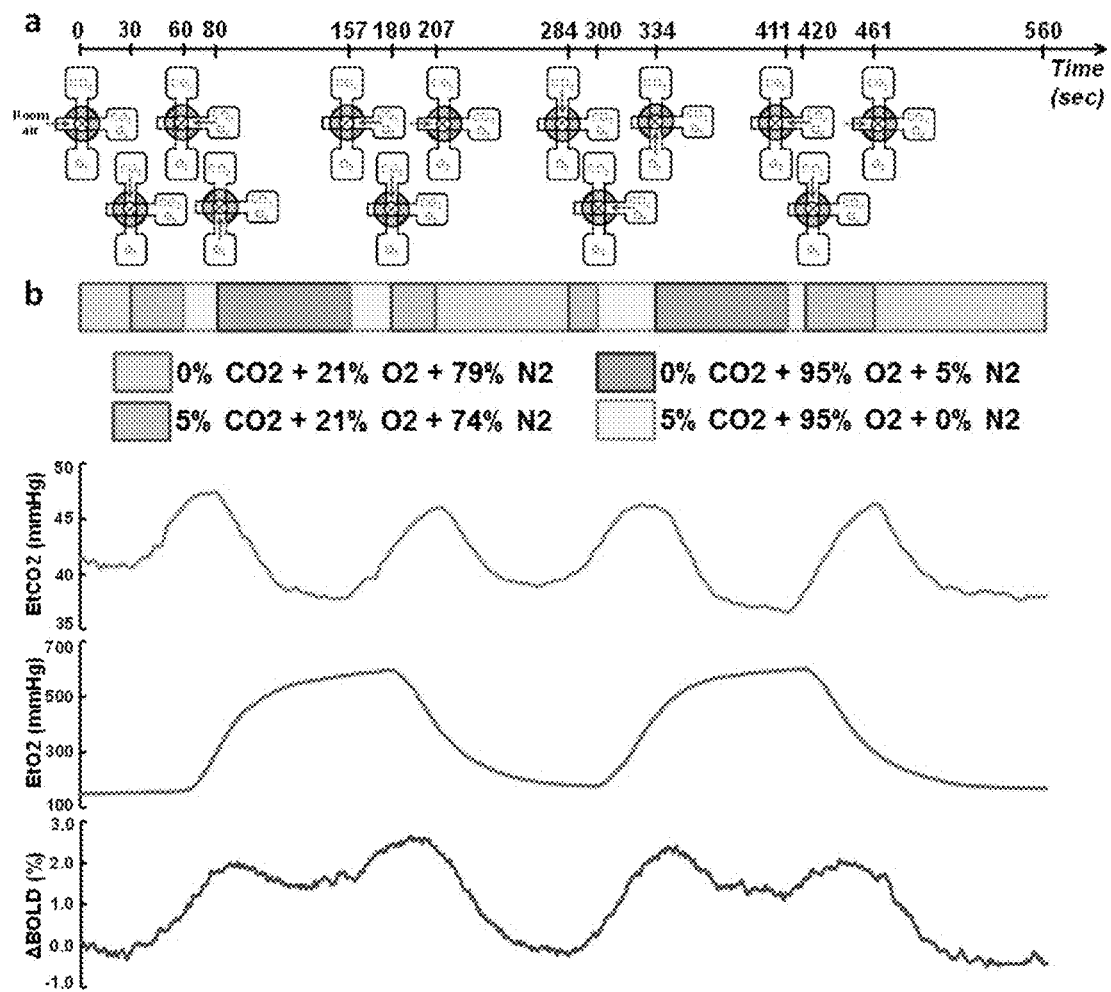
FIG. 4 shows a breathing gas paradigm used with the system of FIG. 1 and example physiological data obtained.

Data was obtained utilizing the CO2 and O2 breathing regimen disclosed in FIG. 4. Seven healthy volunteers (age 26.6±4.6 years, age range 22-34 years, 3 males, 4 females) were scanned in a 3 Tesla MRI scanner (Philips Medical Systems, Best, The Netherlands). Foam padding was placed around the head to minimize motion.

CVR was measured with the concomitant CO2 and O2 paradigm, while BOLD MR images were simultaneously acquired. For comparison purpose, CVR with CO2-only paradigm (5% CO2, 21% O2, and 74% N2), and O2-reactivity with O2-only paradigm (95% O2, and 5% N2) were measured as well in the same MRI session without repositioning the subject.

As a test for its clinical feasibility, concomitant CO2 and O2 paradigm was also applied in one subject (Female, age 64 years) that has been diagnosed with mild cognitive impairment (MCI, early stage of Alzheimer's Disease).

Experimental Data Processing

Data analysis was conducted using in-house MATLAB (MathWorks, Natick, Mass.) scripts. Motion correction was performed by realigning the image volumes of the BOLD scans to their respective first volume within each scan. Then BOLD images from the hypercapnia, hyperoxia and concomitant scans were co-registered by co-registering their mean images, and applying the resulting transformation to each image volume. Next, all the image volumes were smoothed using a Gaussian filter to improve the signal-to-noise ratio. BOLD MR time-courses were normalized to the mean signal during the first room air breathing period.

A frequency analysis method, similar to that used in traveling wave retinotopic mapping (19) and hypercapnia-only CVR mapping (20), was then applied to the gas challenge data. Specifically, a Fast Fourier Transformation (FFT) was applied to the BOLD time-courses on a voxel-by-voxel basis, as well as to the EtCO2 and EtO2 time courses. CVR was determined as the ratio of the BOLD signal magnitude to the EtCO2 magnitude at the CO2 maneuvering frequency ($F_{co2}$). The delay in the cerebrovascular response to CO2 was calculated from the phase difference of the complex FFT data between BOLD signal and EtCO2 at the frequency $F_{co2}$, which was converted into seconds by dividing by $2\pi F_{co2}$. Similarly, O2-reactivity and O2 delay was determined corresponding to the O2 maneuvering frequency.

According to the BOLD fMRI biophysical model (21), CO2-CVR, in the unit of % BOLD signal change per mmHg CO2, is given by Eq. [1] (below), where $$M = TE \cdot A \cdot CBV_0 \cdot (1 - Y_{v,0})^{0.38}$$

M indicates the maximum BOLD signal at a given voxel and is depending on baseline CBV0 at this voxel. Similarly, the O2-reactivity can be written as Eq. [2] (below). By dividing CO2-CVR with O2-reactivity, the M factor is canceled out, so the normalized CVR signal contains minimal CBV effect (Eq. [3] below). Moreover, since $Y_{v,0}$ is relatively constant across the brain as reported by previous literature (22) and $\Delta EtO2$ and $\Delta EtCO2$ are global parameters, normalized CVR should mainly reflect CO2-induced CBF change across voxels.

$$CO2 - CVR = M \cdot f\left(\frac{\Delta CBF}{CBF_0}, \Delta EtCO2\right) \quad [1]$$

$$O2 - \text{reactivity} = M \cdot g(Y_{v,0}, \Delta EtO2) \quad [2]$$

$$\text{Normalized} - CVR = \frac{CO2 - CVR}{O2 - \text{reactivity}} \quad [3]$$

$$= q\left(\frac{\Delta CBF}{CBF_0}, Y_{v,0}, \Delta EtCO2, \Delta EtO2\right)$$

Experimental Results

Figure 5:
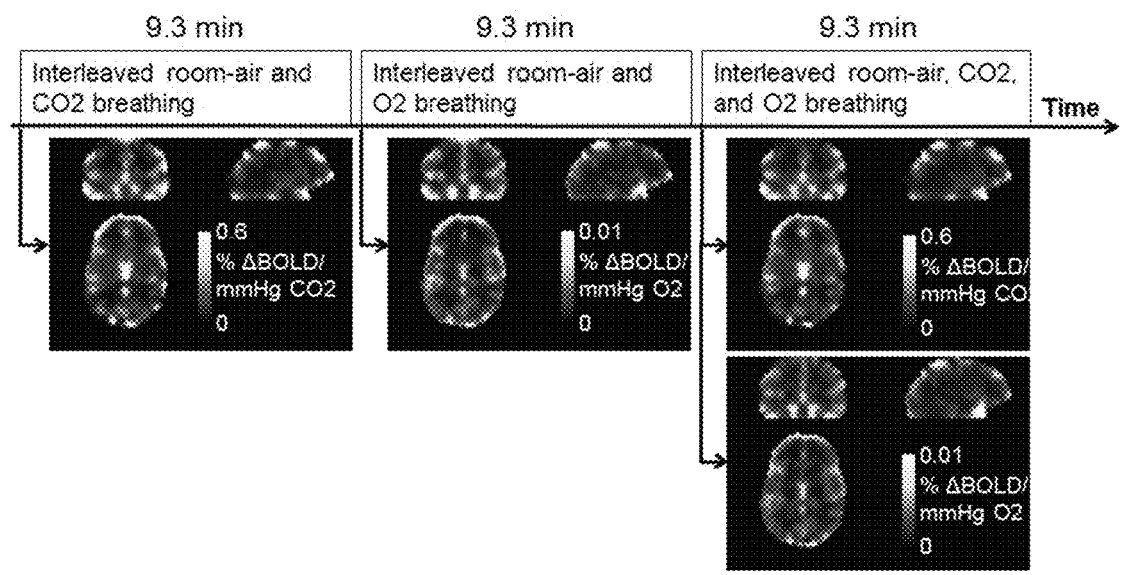
FIG. 5 shows representative CVR maps and O2-reactivity maps obtained using the system of FIG. 1.

With the MRI-compatible gas delivery system as disclosed herein providing the concomitant CO2 and O2 breathing paradigm shown in FIG. 4, a CO2 CVR map can be obtained as well as an O2-reactivity map without additional scan time. FIG. 5 shows the representative results in one subject where three scans of identical duration were performed: a CO2-only challenge, an O2-only challenge, and a concomitant CO2-and-O2 challenge. The comparison between the concomitantly obtained CVR and O2-reactivity maps and the separately obtained maps showed minimal differences.

Figure 6:
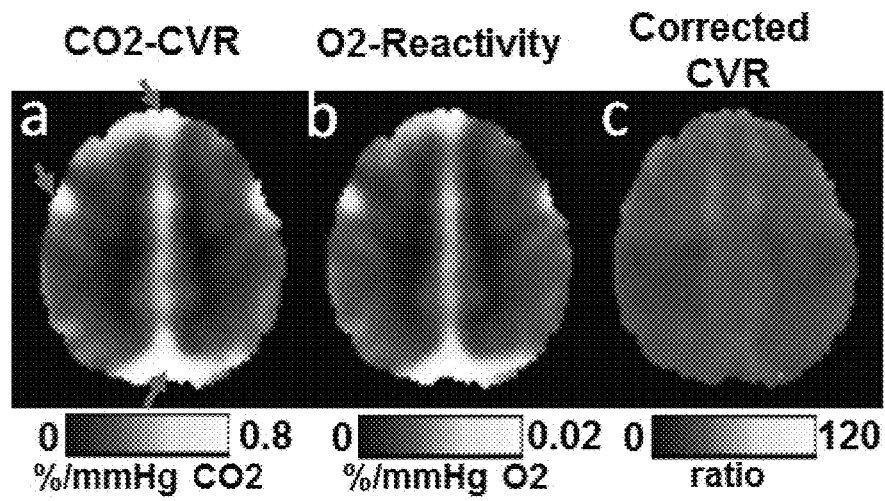
FIG. 6 shows a representative CO2 CVR map, O2-Reactivity map and Corrected CVR map obtained using the paradigm of FIG. 4.

FIG. 6 shows the group-averaged CVR map, O2-reactivity map, and the corrected CVR map. It can be seen that, the CVR map shows very strong contrast in large drains (identified by arrows in FIG. 6A), which may reduce the conspicuity of true CVR abnormalities. These large drains also showed in the O2-reactivity map, which reflects venous blood volume as shown in FIG. 6B. FIG. 6C shows the ratio between CVR and O2-reactivity. In this "Corrected CVR" map shown in FIG. 6C, venous structure is no longer bright, thus it may better depict the true vasodilatory property of the brain.

Figure 7:
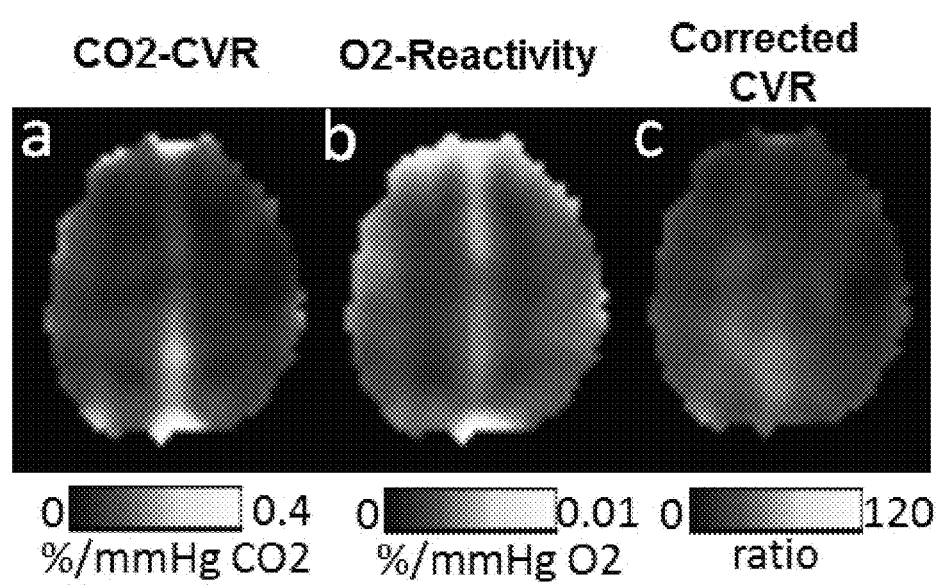
FIG. 7 shows a representative CO2 CVR map, O2-Reactivity map and Corrected CVR map of a Mild Cognitive Impairment (MCI) patient obtained using the paradigm of FIG. 4.

Referring now to FIG. 7, a CVR map and O2 reactivity map was also obtained in the MCI patient. The patient had no difficulty in completing this breathing challenge and reported no adverse effect. It was found that using the O2-reactivity map for correction, the degree and extend of the functional deficit in cerebrovasculature of this patient can be better identified.

This study presented a novel gas delivery system and a novel paradigm with concomitant CO2 and O2 breathing that can be used with MRI to acquire the CVR map and O2-reactivity map of human brain. Experiment results in healthy subjects proved the feasibility of them and the effectiveness of the concomitant breathing design. Preliminary test in a MCI patient demonstrated the clinical applicability of systems and methods disclosed herein.

The presented gas delivery system allows the delivery of special gas mixtures (e.g. any fraction of O2, any fraction of CO2, any fraction of N2, and their combination) to a human for them to breathe while he or she is lying inside the scanner. This system also allows the monitoring and recording of physiological parameters (e.g. end-tidal CO2, end-tidal O2, arterial oxygenation, heart rate, blood pressure) while the gas is being delivered. When this system is used in conjunction with an MRI system, one can obtain a non-invasive measure of vascular and brain health (as illustrated by the human subject data), which can be used by clinicians and researchers to determine the well-being of a patient. Compared to two other MRI-compatible gas delivery systems (17,18), exemplary embodiments of the system disclosed herein are simpler, more economical, easier to use, and more accurate in recording physiological information.

The new breathing paradigm of concomitant CO2 and O2 challenge can produce separate CO2 and O2 reactivity maps within the duration of a single CO2 challenge scan. The O2-reactivity acquired without additional scan time can provide additional information about the venous blood volume, and can also be used to correct the CO2 CVR map by de-emphasized the bright venous signals. In the corrected CVR map, venous structure is no longer bright, thus it may better depict the true vasodilatory property of the brain. This is supported by the data from both the normal subjects and MCI patient.

Exemplary embodiments of the system disclosed herein allow for the delivery of special gas mixtures to a human to breathe while he or she is lying inside the scanner. Also disclosed herein is a sequence and timing of the gas delivery that specifies when and how long O2 and CO2 gas should be delivered in order to produce the informative results without increased scan time. Patients likely to benefit from this system include patients with a high risk for stroke, dementia, atherosclerosis, small vessel diseases, brain tumor, traumatic brain injury, and multiple sclerosis.

All patents, patent applications, and published references cited herein are hereby incorporated by reference in their entirety. While the devices and methods of the present disclosure have been described in connection with the specific embodiments thereof, it will be understood that they are capable of further modification. Furthermore, this application is intended to cover any variations, uses, or adaptations of the devices and methods of the present disclosure, including such departures from the present disclosure as come within known or customary practice in the art to which the devices and methods of the present disclosure pertain.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The terms about, substantially, generally, and approximately (and variations thereof) as used herein, are defined as at least approaching a given state. In specific embodiments, the terms may be defined as being largely but not necessarily wholly what is specified as understood by one of ordinary skill in the art, and in one non-limiting embodiment refers to ranges within 10%, preferably within 5%, more preferably within 1%, and most preferably within 0.5% of what is specified.

Furthermore, all the disclosed elements and features of each disclosed embodiment can be combined with, or substituted for, the disclosed elements and features of every other disclosed embodiment except where such elements or features are mutually exclusive.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

REFERENCES

The following references, to the extent that they provide exemplary procedural or other details supplementary to those set forth herein, are specifically incorporated herein by reference.

REFERENCES

1. Kety S S, Schmidt C F. The Effects of Altered Arterial Tensions of Carbon Dioxide and Oxygen on Cerebral Blood Flow and Cerebral Oxygen Consumption of Normal Young Men. The Journal of clinical investigation 1948; 27(4):484-492.
2. Yezhuvath U S, Uh J, Cheng Y, Martin-Cook K, Weiner M, Diaz-Arrastia R, van Osch M, Lu H. Forebrain-dominant deficit in cerebrovascular reactivity in Alzheimer's disease. Neurobiology of aging 2012; 33(1):75-82.
3. Greenberg S M. Small vessels, big problems. N Engl J Med 2006; 354(14):1451-1453.
4. Fierstra J, Conklin J, Krings T, Slessarev M, Han J S, Fisher J A, Terbrugge K, Wallace M C, Tymianski M, Mikulis D J Impaired peri-nidal cerebrovascular reserve in seizure patients with brain arteriovenous malformations. Brain 2011; 134(Pt 1):100-109.
5. Mikulis D J, Krolczyk G, Desal H, Logan W, Deveber G, Dirks P, Tymianski M, Crawley A, Vesely A, Kassner A, Preiss D, Somogyi R, Fisher J A. Preoperative and postoperative mapping of cerebrovascular reactivity in moyamoya disease by using blood oxygen level-dependent magnetic resonance imaging. J Neurosurg 2005; 103(2):347-355.
6. Donahue M J, Ayad M, Moore R, van Osch M, Singer R, Clemmons P, Strother M. Relationships between hypercarbic reactivity, cerebral blood flow, and arterial circulation times in patients with moyamoya disease. J Magn Reson Imaging 2013; In-press. doi:10.1002/jmri.24070.
7. Mandell D M, Han J S, Poublanc J, Crawley A P, Stainsby J A, Fisher J A, Mikulis D J. Mapping cerebrovascular reactivity using blood oxygen level-dependent MRI in Patients with arterial steno-occlusive disease: comparison with arterial spin labeling MRI. Stroke 2008; 39(7):2021-2028.
8. Mandell D M, Han J S, Poublanc J, Crawley A P, Kassner A, Fisher J A, Mikulis D J. Selective reduction of blood flow to white matter during hypercapnia corresponds with leukoaraiosis. Stroke 2008; 39(7):1993-1998.
9. Lu H, Xu F, Rodrigue K M, Kennedy K M, Cheng Y, Flicker B, Hebrank A C, Uh J, Park D C. Alterations in cerebral metabolic rate and blood supply across the adult lifespan. Cereb Cortex 2011; 21(6):1426-1434.
10. Bandettini P A, Wong E C. A hypercapnia-based normalization method for improved spatial localization of human brain activation with fMRI. NMR Biomed 1997; 10(4-5):197-203.
11. Liau J, Liu T T. Inter-subject variability in hypercapnic normalization of the BOLD fMRI response. Neuroimage 2009; 45(2):420-430.
12. Handwerker D A, Gazzaley A, Inglis B A, D'Esposito M. Reducing vascular variability of fMRI data across aging populations using a breathholding task. Hum Brain Mapp 2007; 28(9):846-859.
13. Thomason M E, Foland L C, Glover G H. Calibration of BOLD fMRI using breath holding reduces group variance during a cognitive task. Hum Brain Mapp 2007; 28(1): 59-68.
14. Liu P, Hebrank A C, Rodrigue K M, Kennedy K M, Park D C, Lu H. A comparison of physiologic modulators of fMRI signals. Hum Brain Mapp 2012; doi:10.1002/hbm.22053. In-press. [PMCID—In process].
15. Davis T L, Kwong K K, Weisskoff R M, Rosen B R. Calibrated functional MRI: mapping the dynamics of oxidative metabolism. Proc Natl Acad Sci USA 1998; 95(4):1834-1839.
16. Hoge R D, Atkinson J, Gill B, Crelier G R, Marren S, Pike G B. Linear coupling between cerebral blood flow and oxygen consumption in activated human cortex. Proc Natl Acad Sci USA 1999; 96(16):9403-9408.
17. Slessarev M, Han J, Mardimae A, Prisman E, Preiss D, Volgyesi G, Ansel C, Duffin J, Fisher J A. Prospective targeting and control of end-tidal CO2 and O2 concentrations. The Journal of physiology 2007; 581(Pt 3):1207-1219.
18. Wise R G, Pattinson K T, Butte D P, Chiarelli P A, Mayhew S D, Balanos G M, O'Connor D F, Pragnell T R, Robbins P A, Tracey I, Jezzard P. Dynamic forcing of end-tidal carbon dioxide and oxygen applied to functional magnetic resonance imaging. Journal of cerebral blood flow and metabolism: official journal of the International Society of Cerebral Blood Flow and Metabolism 2007; 27(8):1521-1532.
19. Engel S A, Rumelhart D E, Wandell B A, Lee A T, Glover G H, Chichilnisky E J, Shadlen M N. fMRI of human visual cortex. Nature 1994; 369(6481):525.
20. Blockley N P, Driver I D, Francis S T, Fisher J A, Gowland P A. An improved method for acquiring cerebrovascular reactivity maps. Magnetic resonance in medicine: official journal of the Society of Magnetic Resonance in Medicine/Society of Magnetic Resonance in Medicine 2011; 65(5):1278-1286.
21. Hodge, et al. Linear coupling between cerebral blood flow and oxygen consumption in activated human cortex. PNAS 96:9403-9408, 1999.
22. Raichle et al. A default mode of brain function. PNAS 98:676-682, 2001.

The invention claimed is:
1. A system for administering breathing gasses to a subject during a magnetic resonance imaging (MRI) scan, the system comprising:
 a plurality of containers containing one or more gasses, wherein the plurality of containers are comprised of flexible non-metallic containers;
 a multi-port valve in fluid communication with the plurality of containers, wherein the plurality of containers supply the one or more gasses to the multi-port valve;
 a two-way non-rebreathing valve;
 a conduit in fluid communication with the multi-port valve and the two-way non-rebreathing valve;

a tube in fluid communication with the two-way non-rebreathing valve, a first sampling port and a second sampling port; and
a mouthpiece in fluid communication with the tube.

2. The system of claim 1 wherein:
at least one of the containers contains 5% CO2 and 95% O2;
at least one of the containers contains 5% N2 and 95% N2; and
at least one of the containers contains 5% CO2, 21% O2 and 74% N2.

3. The system of claim 1 further comprising a coupling mechanism configured couple to an MRI coil, wherein the coupling mechanism is configured to support the mouthpiece, the two-way breathing valve, and the tube from the MRI head coil.

4. The system of claim 3 wherein the coupling mechanism is configured to couple the conduit to the MRI head coil.

5. The system of claim 1 wherein the tube is a U-shaped tube.

6. The system of claim 1 wherein the multi-port valve can be adjusted during use to adjust a mixture of the one or more gasses in fluid communication with the conduit.

7. The system of claim 1 wherein the one or more gasses comprises O2, CO2 and N2.

8. The system of claim 1 wherein the first sampling port is coupled to an O2 monitor and the second sampling port is coupled to a CO2 monitor.

9. The system of claim 8 wherein the O2 monitor is configured to measure end-tidal O2 levels and the CO2 monitor is configured to measure end-tidal CO2 levels, and wherein the end-tidal O2 level is measured independent of the end-tidal CO2 level.

10. The system of claim 1 wherein the multi-port valve is configured to allow room air to enter a port in the multi-port valve.

11. The system of claim 1 further comprising a nose clip.

12. The system of claim 1 further comprising a first elbow coupling member coupled to the mouthpiece and the tube.

13. The system of claim 1 further comprising a second elbow coupling member coupled to the two-way non-rebreathing valve and the tube.

14. A method comprising:
administering breathing gasses to a subject during a magnetic resonance imaging (MRI) scan; and
monitoring a plurality of physiological parameters of the subject during the MRI scan, wherein the breathing gasses are administered to the patient via a system comprising:
a plurality of containers containing one or more gasses, wherein the plurality of containers are comprised of flexible non-metallic containers;
a multi-port valve in fluid communication with the plurality of containers, wherein the plurality of containers supply the one or more gasses to the multi-port valve;
a two-way non-rebreathing valve;
a conduit in fluid communication with the multiport valve and the two-way non-rebreathing valve;
a tube in fluid communication with the two-way non-rebreathing valve, a first sampling port and a second sampling port; and
a mouthpiece in fluid communication with the tube.

15. The method of claim 14 wherein administering breathing gasses to a subject comprises administering gasses containing the following mixtures:
5% CO2 and 95% O2;
5% N2 and 95% N2; and
5% CO2, 21% O2 and 74% N2.

16. The method of claim 14 further comprising coupling a coupling mechanism to an MRI head coil to support the mouthpiece, the two-way breathing valve, and the tube from the MRI head coil.

17. The method of claim 16 further comprising coupling the conduit to the MRI head coil with the coupling mechanism.

18. The method of claim 14 wherein the tube is a U-shaped tube.

19. The method of claim 14 further comprising adjusting the multi-port valve to adjust a mixture of the one or more gasses in fluid communication with the conduit.

20. The method of claim 14 wherein the one or more gasses comprises O2, CO2 and N2.

21. The method of claim 20 wherein O2 and CO2 gasses are applied concomitantly.

22. The method of claim 14 further comprising applying a nose clip to the subject to restrict the subject from breathing through his or her nose.

23. The method of claim 14 wherein a facemask is not applied to the subject.

24. The method of claim 14 wherein the first sampling port is coupled to an O2 monitor and the second sampling port is coupled to a CO2 monitor.

25. The method of claim 24 further comprising measuring end-tidal O2 levels and measuring end-tidal CO2 levels, wherein the end-tidal O2 level is measured independently of the end-tidal CO2 level.

26. The method of claim 25 further comprising:
generating a CO2 reactivity map; and
generating an O2 reactivity map.

27. The method of claim 26 further comprising:
using the CO2 reactivity map as a surrogate of cerebrovascular reactivity or cerebrovascular reserve for disease diagnosis and/or monitoring; and
using the O2 reactivity map as a surrogate of cerebral blood volume for disease diagnosis and/or monitoring.

28. A method comprising:
administering breathing gasses to a subject during a magnetic resonance imaging (MRI) scan;
monitoring a plurality of physiological parameters of the subject during the MRI scan, wherein the breathing gasses are administered to the patient via a system comprising:
a plurality of containers containing one or more gasses;
a multi-port valve in fluid communication with the plurality of containers;
a two-way non-rebreathing valve;
a conduit in fluid communication with the multiport valve and the two-way non-rebreathing valve;
a tube in fluid communication with the two-way non-rebreathing valve, a first sampling port and a second sampling port; and
a mouthpiece in fluid communication with the tube, wherein the first sampling port is coupled to an O2 monitor and the second sampling port is coupled to a CO2 monitor;
measuring end-tidal O2 levels and measuring end-tidal CO2 levels, wherein the end-tidal O2 level is measured independently of the end-tidal CO2 level;
generating a CO2 reactivity map;
generating an O2 reactivity map; and using the O2 reactivity map to normalize a CVR map to obtain a corrected CVR map.

* * * * *